United States Patent [19]

Munro

[11] Patent Number: 4,994,616
[45] Date of Patent: Feb. 19, 1991

[54] ANILIDE HERBICIDES

[75] Inventor: David Munro, Maidstone, United Kingdom

[73] Assignee: UBE Industries, Ltd., Yamaguchi, Japan

[21] Appl. No.: 180,576

[22] Filed: Apr. 12, 1988

[30] Foreign Application Priority Data

May 1, 1987 [GB] United Kingdom ................ 8710362

[51] Int. Cl.$^5$ ................. C07C 213/00; C07C 215/00; C07C 217/00
[52] U.S. Cl. .................................... 564/346; 564/347; 564/352; 564/353
[58] Field of Search ............... 564/346, 347, 352, 353; 71/94, 118

[56] References Cited

U.S. PATENT DOCUMENTS 4,257,801 3/1981 Barton et al. ............................ 71/70
4,465,507 8/1984 Konno et al. ............................ 71/98

FOREIGN PATENT DOCUMENTS 53011 6/1982 European Pat. Off. .
239414 9/1987 European Pat. Off. .
56-057752 5/1981 Japan .
57-014506 1/1982 Japan .
60-258150 12/1985 Japan .
2024213 1/1980 United Kingdom .
2108498 5/1983 United Kingdom .

Primary Examiner—Nathan M. Nutter

[57] ABSTRACT

A novel herbicide of formula I

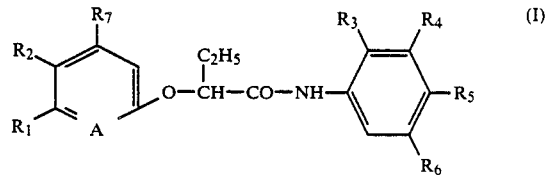

wherein $R_1$ represents a halogen atom or an alkyl, haloalkoxy, haloalkyl or alkoxycarbonyl group;
$R_2$ represents a hydrogen or halogen atom;
each of $R_3$ to $R_6$ independently represents a hydrogen or halogen atom or a cyano, alkyl, haloalkyl, alkoxy or haloalkoxy group;
$R_7$ represents a hydrogen or halogen atom, or an alkyl, haloalkoxy, haloalkyl or alkoxycarbonyl group;
and A represents a nitrogen atom or a —CH— group, together with its formulation and use as a herbicide, and its preparation.

5 Claims, No Drawings

ANILIDE HERBICIDES

This invention relates to certain novel phenoxy anilide compounds, to their use as herbicides, and to their preparation.

According to the present invention there is provided a compound of formula I

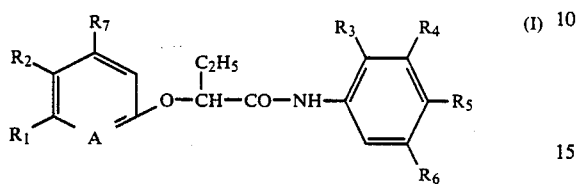

wherein $R_1$ represents a halogen atom or an alkyl, haloalkoxy, haloalkyl or alkoxycarbonyl group;

$R_2$ represents a hydrogen or halogen atom;

$R_7$ represents a hydrogen or halogen atom, or an alkyl, haloalkoxy, haloalkyl or alkoxycarbonyl group;

each of $R_3$ to $R_6$ independently represents a hydrogen or halogen atom or a cyano, alkyl, haloalkyl, alkoxy or haloalkoxy group;

and A represents a nitrogen atom or a —CH— group.

Unless otherwise stated in this specification an alkyl, haloalkyl, alkoxy or haloalkoxy group suitably has 1-6 carbon atoms, preferably 1-4. A halogen atom is preferably fluorine or chlorine. A haloalkyl or haloalkoxy group is preferably substituted by 1-3 halogen atoms, preferably fluorine or chlorine; and is preferably trifluoromethyl or trifluoromethoxy.

One preferred group of compounds according to the invention is represented by formula I where A represents a —CH— group, $R_1$ represents a halogen atom or a haloalkoxy or haloalkyl group and $R_7$ represents a hydrogen atom.

Preferably $R_1$ represents a chlorine atom or a trifluoromethyl, difluoromethoxy or acetoxy group.

$R_2$ preferably represents a hydrogen, fluorine or chlorine atom.

$R_3$ preferably represents a hydrogen, fluorine or chlorine atom.

$R_4$ preferably represents a hydrogen or chlorine atom or a trifluoromethyl group.

$R_5$ preferably represents a hydrogen, fluorine or chlorine atom, or an alkyl group.

$R_6$ preferably represents a hydrogen or fluorine atom or an alkyl, alkoxy or trifluoromethyl group.

$R_7$ preferably represents a hydrogen atom or an alkyl or trifluoromethyl group.

Preferably, at least one of $R_3$ and $R_5$ represents a chlorine or fluorine atom. Most preferably $R_3$ represents a chlorine or, especially, a fluorine atom and $R_5$ represents a hydrogen atom or a chlorine or fluorine atom, or an alkyl group.

A further preferred group of compounds according to the invention is represented by formula I in which $R_1$ represents a trifluoromethyl group, $R_2$ represents a chlorine or fluorine atom, $R_3$ and $R_5$ each represent a fluorine atom, $R_4$ and $R_6$ each represent a hydrogen atom and A represents a group —CH—.

It will be appreciated that compounds of formula I can exist in stereoisomeric forms. The present invention is intended to include different stereoisomers of the compounds of formula I, their mixtures and herbicidal compositions containing the active ingredient in a particular isomeric form.

According to a further aspect of the invention there is provided a process for the preparation of a compound of formula I, which comprises reacting a compound of formula II

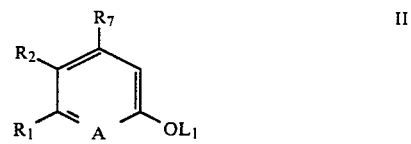

, where $R_1$, $R_2$ and $R_7$ are as defined above and $L_1$ represents a hydrogen or alkali metal atom or a group —CH($C_2H_5$)COX where X is a leaving group, with a compound of formula III

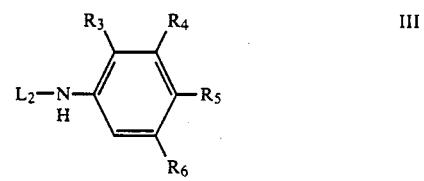

, where $R_3$, $R_4$, $R_5$ and $R_6$ are as defined above and where, when $L_1$ represents hydrogen or an alkali metal atom, $L_2$ represents a group —COCH($C_2H_5$)Y where Y is a leaving group or, when $L_1$ represents a group —CH($C_2H_5$)COX, $L_2$ represents a hydrogen atom.

Thus in one preferred process of the invention, compound II is an alkali metal salt which is reacted with a compound of formula III where $L_2$ is —COCH($C_2H_5$)Y where Y is a leaving group, for example a chlorine or, especially, a bromine atom or a mesyloxy or tosyloxy group. The reaction of such compounds of formulae II and III is preferably carried out in a suitable solvent, for example, dimethyl sulphoxide, sulpholane, dimethyl formamide, dimethyl acetamide or tetrahydrofuran at elevated temperature, for example 40° to 150° C., conveniently under reflux, and preferably under an inert atmosphere such as nitrogen.

Compounds of formula III where $L_2$ is —COCH($C_2H_5$)Y are suitably prepared by reacting an appropriately 2-substituted butyric acid, for example 2-bromobutyric acid when Y in the compound of formula III is to be a bromine atom, with thionyl chloride or bromide, at 50°-100° C. in the presence of a hydrocarbon solvent, for example benzene or toluene, under dry nitrogen; and reacting the resulting acid chloride or bromide with an aniline of formula

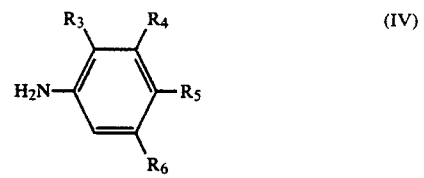

suitably at a temperature in the range of 10°-50° C. conveniently at ambient temperature, in the presence of a hydrocarbon solvent and pyridine or triethylamine.

Alternatively the 2-bromo butyric acid is reacted with N-methylmorpholine and isobutylchloroformate, suitably in the presence of an organic solvent such as tetrahydrofuran under nitrogen at a temperature below 0° C. followed by reaction with an aniline of formula (IV), suitably at a temperature below 0° C.

In an alternative route employing similar chemistry an appropriately substituted phenol may be reacted, under similar conditions for the reaction of compound of formula II and III, with a butyric acid, substituted at the 2-position by a leaving group X, preferably a bromine or chlorine atom or a mesyloxy or tosyloxy group, to yield a corresponding 2-phenoxybutyric acid, which is then treated with thionyl chloride or bromide, to form the acid chloride or bromide, the product then being treated with an aniline of formula IV, these reactions taking place under similar conditions to those described above for the preparation of compounds of formula III. Alternatively, where A is N, the appropriate 2-halopyridine may be reacted with an alkali metal salt of a butyric acid having a leaving group, suitably a hydroxy group, at the 2-position, in the presence of a solvent, such as dimethylformamide, and sodium hydride, for example at ambient temperature, followed by treatment with thionyl chloride or bromide and an aniline of formula IV as described above.

The starting materials are either known by or may be prepared from known compounds by standard techniques. It has been found advantageous to prepare the compounds of formula II where $L_1$ is hydrogen from corresponding anilines by preparation therefrom of diazonium salts, and hydrolysis thereof, suitably by preparation of the diazonium sulphate then its hydrolysis in a refluxing solution of copper sulphate, under steam distillation.

It has been discovered that compounds of the general formula I have advantageous herbicidal activity in comparison with compounds of closely similar structure. Therefore the invention further provides a herbicidal composition comprising a compound of formula I as defined above in association with at least one carrier, and a method of making such a composition, which comprises bringing a compound of formula I into association with at least one carrier.

The invention also provides the use of such a compound or composition according to the invention as a herbicide. Further, in accordance with the invention there is provided a method of combating undesired plant growth at a locus by treating the locus with a compound or composition according to the invention. The locus may for example be a crop area, for example a crop area containing plants or seeds of maize, oat, linseed, mustard, soya, wheat, barley, and rice (including paddy rice). Application to the locus may be pre-emergence or post-emergence. The dosage of active ingredient used may, for example, be from 0.01 to 10 kg/ha, preferably 0.05 to 4kg/ha. A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating herbicidal compositions may be used. Preferably compositions according to the invention contain 0.5 to 95% by weight of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating herbicidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminum silicates, for example attapulgites and vermiculites; aluminium silicates, for example kaolinites, montomorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilizers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0-10% w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½-10% w of active ingredient. Granules are usually prepared to have a size between 10 and 100 BS mesh (1.676-0.152 mm), and may be manufactured by agglomeration or impregnation techniques. Generally, granules will contain ½-75% w active ingredient and 0-10% w of additives such as stabilizers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10-50% w/v active ingredient, 2-20% w/v emulsifiers and 0-20% w/v of other additives such as stabilizers, penetrants and corrosion inhibitors. Suspension concentrates are usually compounded so as to obtain a stable, non-sedimenting flowable product and usually contain 10-75% w active ingredient, 0.5-15% w of dispersing agents, 0.1-10% w of suspending agents such as protective colloids and thixotropic agents, 0-10% w of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

The composition of the invention may also contain other ingredients, for example other compounds possessing herbicidal, insecticidal or fungicidal properties. The invention will now be further described with reference to the following Examples. The compounds were characterized by mass spectometry (M/e), CHN analysis and, when the compounds were solids, by melting point.

EXAMPLE 1

Preparation of 2-(3-trifluoromethylphenoxy)butyric acid anilide (a) 2-Bromobutyric acid (50 g) was dissolved in dry benzene (100 ml). Thionyl chloride (50 g) was added dropwise with stirring under dry nitrogen under reflux. After 1 hour, the solvent was removed in vacuo to give 2-bromobutyric acid chloride (53 g) as a colorless oil.

(b) 10 g of 2-bromobutyric acid chloride was added dropwise with stirring at ambient temperature to a stirred solution of aniline (5 g) and triethylamine (10 g) in dry benzene (100 ml). The reaction mixture was filtered and the filtrate purified by thin layer chromatography on silica, using chloroform-ethylacetate (90-10 by volume) to give a colorless oil which solidified. Recrystallization from hexane-ethylacetate gave 2-bromobutyric acid anilide (10.1 g), as colorless crystals, mp 99° C.

(c) 3-Trifluoromethylphenol (3 g) was added dropwise to a suspension (30 ml) of oil-free sodium hydride (0.5 g) in dry tetrahydrofuran with stirring, under dry nitrogen. After 30 minutes, a solution of 2-bromobutyric acid anilide (4.5 g) in dry tetrahydrofuran (20 ml) was added dropwise and the reaction mixture refluxed for 1 hour. Most of the solvent was removed in vacuo. Chloroform-water (300 ml, 50-50 by volume) was added, and the organic layer was separated, dried and chromatographed to give a colorless oil which solidified. Recrystallization gave the title compound as colorless crystals, (4.6 g, mp 115° C.).

| Analysis | | | |
|---|---|---|---|
| Calculated | 63.2% C | 5.0% H | 4.3% N |
| Found | 63.4% C | 5.0% H | 4.4% N |

The following compounds in Table I below were prepared in analogous manner to Example 1, in some cases from 2- bromobutyric acid bromide.

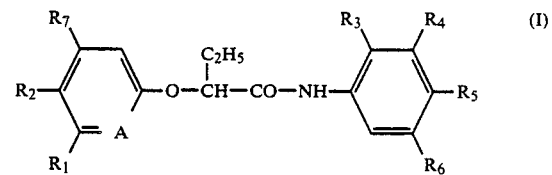

(I)

| Example No. | $R_1$ | $R_2$ | $R_3$ | $R_4$ | $R_5$ | $R_6$ | $R_7$ | A | mp (°C.) | C | H | N |
|---|---|---|---|---|---|---|---|---|---|---|---|---|
| 2 | $CF_3$ | Cl | F | H | F | H | H | CH | 85 | 51.8/51.8 | 3.3/3.4 | 3.6/3.7 |
| 3 | $CF_3$ | H | F | H | F | H | H | CH | 84 | 59.8/59.4 | 4.4/4.2 | 4.1/3.9 |
| 4 | $CF_3$ | H | F | H | F | H | H | CH | 80 | 56.8/56.8 | 3.9/4.0 | 3.9/3.9 |
| 5 | $CF_3$ | H | H | H | F | H | H | CH | 90 | 59.8/60.4 | 4.4/4.3 | 4.1/4.0 |
| 6 | $CF_3$ | F | F | H | F | H | H | CH | 59 | 54.1/53.9 | 3.5/3.7 | 3.7/4.1 |
| 7 | $CF_3$ | H | H | F | H | H | H | CH | 90 | 59.8/59.9 | 4.4/4.4 | 4.1/3.9 |
| 8 | $CF_3$ | H | H | H | Cl | H | H | CH | 69 | 57.1/56.9 | 4.2/4.2 | 3.9/3.9 |
| 9 | $CF_3$ | F | Cl | H | Cl | H | H | CH | 98 | 38.6/38.9 | 3.2/3.2 | 4.5/4.3 |
| 10 | $CF_3$ | F | H | Cl | Cl | H | H | CH | 100 | 49.8/49.8 | 3.2/3.3 | 3.4/3.7 |
| 11 | $CF_3$ | F | H | $CF_3$ | H | H | H | CH | 175/1.5 mm Hg | 52.8/52.7 | 3.3/3.4 | 3.4/3.7 |
| 12 | $CF_3$ | F | F | H | H | $CF_3$ | H | CH | 160/1.0 mm Hg | 50.6/49.9 | 3.0/3.2 | 3.3/3.3 |
| 13 | $CF_3$ | F | F | H | H | $CH_3$ | H | CH | 97 | 57.9/57.7 | 4.3/4.3 | 3.7/3.7 |
| 14 | $CF_3$ | F | F | H | H | F | H | CH | 81 | 54.1/53.8 | 3.5/3.3 | 3.7/3.6 |
| 15 | $CF_3$ | F | Cl | H | Cl | $O$-$i$-$C_3H_7$ | H | CH | 180/1.5 mm Hg | 51.3/51.0 | 4.1/4.1 | 3.8/3.8 |
| 16 | $CF_3$ | Cl | H | H | $i$-$C_3H_7$ | H | H | CH | 170/1.5 mm Hg | 60.1/59.8 | 5.2/5.5 | 3.5/3.9 |
| 17 | $CF_3$ | Cl | H | H | H | H | H | CH | 152 | 57.1/56.8 | 4.2/4.4 | 3.9/4.0 |
| 18 | $CF_3$ | F | F | H | F | F | H | CH | 95 | 51.6/50.9 | 3.0/2.9 | 3.6/3.4 |

-continued

| Example No. | $R_1$ | $R_2$ | $R_3$ | $R_4$ | $R_5$ | $R_6$ | $R_7$ | A | mp (°C.) | CHN Analysis Calculated/Found % | | |
|---|---|---|---|---|---|---|---|---|---|---|---|---|
| | | | | | | | | | | C | H | N |
| 19 | $CF_3$ | F | F | H | $CH_3$ | H | H | CH | 94 | 57.9/57.7 | 4.3/4.5 | 3.7/3.7 |
| 20 | $CF_3$ | F | F | H | Cl | H | H | CH | 95 | 51.9/51.9 | 3.3/3.0 | 3.6/3.5 |
| 21 | $OCHF_2$ | H | F | H | F | H | H | CH | 68 | 57.1/56.8 | 4.2/4.2 | 3.9/3.7 |
| 22 | Cl | H | F | H | F | H | H | CH | 77 | 59.0/59.0 | 4.3/4.4 | 4.3/4.2 |
| 23 | Cl | F | F | H | F | H | H | CH | 94 | 55.9/56.0 | 3.8/3.9 | 4.1/4.4 |
| 24 | Cl | Cl | F | H | F | H | H | CH | 109 | 53.3/53.1 | 3.6/3.6 | 3.9/4.0 |
| 25 | $CH_3COO$ | H | F | H | F | H | H | CH | bp 200° C.; 1.5 mm Hg | 61.9/61.6 | 4.9/4.9 | 4.0/4.4 |
| 26 | $CF_3$ | H | F | H | F | H | $CF_3$ | CH | 91 | 51.6/51.7 | 3.0/3.3 | 3.3/3.5 |
| 27 | $CH_3$ | Cl | F | H | F | H | H | CH | 95 | 60.1/60.4 | 4.7/4.8 | 4.1/4.3 |
| 28 | $CH_3$ | Cl | F | H | F | H | $CH_3$ | CH | 99 | 61.1/61.2 | 5.1/5.2 | 4.0/4.3 |

EXAMPLE 29

Preparation of S(-)-2-(3-fluoro-4-trifluoromethyl phenoxy)butyric acid 2, 4-difluoroanilide (a) D-2-aminobutyric acid (12 g) and potassium bromide (50 g) were dissolved in 2.5N sulphuric acid (275 ml). After cooling to −10° C., sodium nitrite (12.6 g) was added during 1 hour, keeping the temperature at −5° C. After stirring for 1.5 hours at about −5° C., the mixture was extracted with ethyl acetate, the organic phase dried and chromatographed to give as a colorless oil D-2-bromobutyric acid (13.2 g).

(b) A solution of D-2-bromobutyric acid (10 g) (prepared as in (a) above) in dry tetrahydrofuran (100 ml) was cooled to −15° C. under nitrogen and treated sequentially with N-methyl morpholine (6.6 ml) and isobutylchloroformate (8 ml), then stirred for about 1 minute at −15° C. To this mixture was added 2, 4-difluoroaniline (7.8 g) and the solution stirred at −15° C. for 30 minutes. A 10% (by weight) solution of citric acid (300 ml) was added and the mixture extracted with ethylacetate, the organic layer washed with saturated sodium bicarbonate solution and chromatographed to give a colorless oil which solidified and was recrystallized to give colorless crystals mp 92°–4° C. (4.6 g) of D-2-bromobutyric acid 2, 4-difluoroanilide.

(c) The anilide prepared in (b) (4 g) and 3-trifluoromethyl-4-fluorophenol (3 g) were added to dry dimethylformamide (20 ml). Dry potassium carbonate (4 g) was added with stirring under dry nitrogen. The reaction mixture was stirred at about 110° C. for 30 minutes. Most of the dimethyl formamide was removed in vacuo and a mixture of equal volumes of water and chloroform (300 ml) added to the residue. The organic layer was separated, washed, dried and chromatographed to give a colorless oil which solidified and was recrystallized from hexane to give colorless crystals mp 89° C. of the title compound (3.2 g). $[\alpha]_D^{25} = -11(CH_3OH)$.

EXAMPLE 30

Preparation of R (+) -2-(3-fluoro-4-trifluoromethylphenoxy)butyric acid 2, 4-difluoroanilide Using a procedure similar to Example 29 (a) but employing L-2-aminobutyric acid, there was obtained as a colorless oil L-2-bromobutyric acid (11 g), which was reacted as described in Example 29 (b) to yield L-2-bromobutyric acid 2, 4-difluoroanilide of mp 92°–94° C. (4.8 g). This compound was reacted as described in Example 29 (c) to give a colorless oil which was recrystallized from hexane to give colorless crystals, mp 89° C., of the title compound (3.4 g). $[\alpha]_D^{25} = +11(CH_3OH)$.

EXAMPLE 31

Preparation of 2-(6-trifluoromethyl-2-pyridinyloxy)butyric acid 2, 4-difluoroanilide (a) 2-hydroxybutyric acid sodium salt (10 g) was added to dry dimethylformamide (100 ml) and oil free sodium hydride (2 g) added in a single portion with stirring under nitrogen. The reaction mixture was stirred at ambient temperature for 30 minutes and then at about 80° C. for 10 minutes prior to addition of 2-chloro-6-trifluoromethylpyridine (10 g). The reaction mixture was then heated to 100–110° C. for 1 hour. The mixture was poured into an equal volume mixture of water and chloroform (1 liter) and the original layer made just acidic (pH4), followed by vigorous extraction into the organic phase which was separated, washed and dried. Chromatography gave a colorless solid which was recrystallized from hexane to give colorless crystals mp. 118° C. (11.9 g) of 2-(6-trifluoromethyl-2-pyridinyloxy)butyric acid.

(b) The compound prepared in (a) above (3 g) was dissolved in toluene (25 ml) and thionyl chloride (3 ml) added. The reaction mixture was heated at 110° C. with stirring under nitrogen for 1 hour, before removal of solvent in vacuo. The residue was redissolved in fresh toluene (10 ml) and added dropwise with stirring under nitrogen to a solution of 2, 4-difluoroaniline (1.5 g) and triethylamine (2 g) in toluene (20 ml). The mixture was refluxed for 10 minutes and the precipitated amine hydrochloride removed by filtration. The product was isolated by evaporation of the filtrate and the residue chromatographed. Chromatography gave a colorless oil which solidified and was recrystallized from hexane to give colorless crystals, mp 91° C., of the title compound (3.2 g).

| Analysis | | | |
|---|---|---|---|
| Calculated | 53.3% C | 3.6% H | 7.8% N |
| Found | 53.3% C | 3.7% H | 7.8% N |

HERBICIDAL ACTIVITY

EXAMPLE B1

To evaluate their herbicidal activity, compounds according to the invention were tested using a representative range of plants: maize, Zea mays (Mz); rice, Oryza sativa (R); barnyard grass, Echinochloa crusgalli (BG); oat, Avena sativa (0); linseed, Linum usitatissimum (L);

mustard, *Sinapsis alba* (M); sugar beet, *Beta vulgaris* (SB) and soya bean, *Glycine max* (S).

The tests fall into two categories, pre-emergence and post-emergence. The pre-emergence tests involved spraying a liquid formulation of the compound onto the soil in which the seeds of the plant species mentioned above had recently been sown. The post-emergence tests involved two types of test, viz., soil drench and foliar spray tests. In the soil drench tests the soil in which the seedling plants of the above species were growing was drenched with a liquid formulation containing a compound of the invention, and in the foliar spray tests the seedling plants were sprayed with such a formulation.

The soil used in the tests was a prepared horticultural loam.

The formulations used in the tests were prepared from solutions of the test compounds in acetone containing 0.4% by weight of an alkylphenol/ethylene oxide condensate available under the trade mark TRITON X-155. These acetone solutions were diluted with water and the resulting formulations applied at dosage levels corresponding to 5 kg or 1 kg of active material per hectare in a volume equivalent to 900 liters per hectare in the soil spray and foliar spray test, and at a dosage of level equivalent to 10 kilograms of active material per hectare in a volume equivalent to approximately 3,000 liters per hectare in the soil drench tests.

In the pre-emergence tests untreated sown soil and in the post-emergence tests untreated soil bearing seedling plants were used as controls.

The herbicidal effects of the test compounds were assessed visually twelve days after spraying the foliage and the soil, and thirteen days after drenching the soil and were recorded on a 0–9 scale. A rating 0 indicated growth as untreated control, whilst a rating 9 indicates death. An increase of 1 unit on the linear scale approximates to a 10% increase in the level of effect. The symbol * indicates that testing was not effected, for example because there was insufficient compound for all tests. A blank space denotes a rating 0.

The effect of the compounds of the present invention on plants appears to increase over time. Therefore the herbicidal effects of some of the compounds were additionally assessed 19 days after treatment (19 d.a.t.).

The results of the tests are set out in Table 2 below, in which the compounds are identified by reference to the preceding examples.

TABLE 2

| Compound of Ex. No. | Soil drench 10/kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 1 | | | | | | | | | 5 | 1 | 3 | 3 | 6 | 7 | 6 | 4 | | | 4 | 7 | | | 6 | 8 | 7 | 3 |
| | | | | | | | | | 1 | 1 | 3 | 3 | 5 | 5 | 4 | 3 | | | 4 | | | 2 | 5 | 6 | |
| 2 | 2 | 4 | 5 | 6 | | 4 | 4 | | 5 | 4 | 4 | 8 | 6 | 7 | 7 | 8 | 7 | 5 | 4 | 8 | 7 | 5 | 8 | 9 | 3 |
| | | | | | | | | | 1 | 3 | 2 | 6 | 4 | 6 | 7 | 7 | 6 | 3 | 2 | 8 | 5 | 3 | 7 | 8 | 2 |
| 2 (19 d.a.t.) | 1 | 4 | 4 | 5 | | 5 | 4 | | 5 | 3 | 4 | 9 | 7 | 9 | 9 | 9 | 7 | 4 | 4 | 9 | 6 | 3 | 9 | 9 | 3 |
| | | | | | | | | | 1 | 2 | 1 | 8 | 4 | 8 | 9 | 8 | 5 | 2 | 1 | 9 | 5 | 1 | 8 | 8 | 2 |
| 3 | 1 | | 3 | | | | 3 | 2 | 5 | 2 | | 7 | 5 | 9 | 7 | 7 | 7 | 2 | 5 | 9 | 4 | 3 | 6 | 7 | |
| | | | | | | | | | 1 | 2 | | 6 | 4 | 7 | 7 | 6 | 5 | 1 | 1 | 7 | 1 | | 3 | 4 | |
| 4 | | 3 | 6 | 4 | 2 | 3 | 3 | | 5 | 7 | 3 | 7 | 6 | 6 | 7 | 7 | 7 | 2 | 7 | 9 | 7 | 5 | 8 | 8 | 4 |
| | | | | | | | | | 1 | 3 | 1 | 6 | 3 | 5 | 6 | 6 | 6 | 1 | 5 | 9 | 6 | 3 | 7 | 8 | 2 |
| 4 (19 d.a.t.) | | 3 | 6 | 4 | 2 | 6 | 3 | 1 | 5 | 6 | 2 | 8 | 5 | 6 | 9 | 8 | 7 | 2 | 5 | 9 | 6 | 4 | 9 | 9 | 4 |
| | | | | | | | | | 1 | 3 | | 7 | 3 | 5 | 7 | 8 | 5 | 1 | 3 | 9 | 5 | 3 | 9 | 9 | 2 |
| 5 | 2 | 3 | 5 | 3 | 4 | 5 | 5 | | 5 | 4 | 4 | 8 | 5 | 9 | 7 | 8 | 7 | 2 | 2 | 9 | 5 | 4 | 8 | * | 1 |
| | | | | | | | | | 1 | 2 | 2 | 6 | 4 | 7 | 6 | 7 | 6 | 1 | | 8 | 3 | | 7 | * | |
| 5 (19 d.a.t.) | 3 | 3 | 7 | 3 | 4 | 5 | 5 | | 5 | 3 | 3 | 8 | 3 | 9 | 9 | 8 | 8 | 1 | 3 | 9 | * | 4 | 8 | 9 | 2 |
| | | | | | | | | | 1 | 2 | 2 | 6 | 3 | 7 | 8 | 7 | 6 | | | 9 | 3 | 1 | 8 | 9 | |
| 6 | 3 | 4 | 6 | 6 | 2 | 4 | 6 | 3 | 5 | 4 | 4 | 7 | 5 | 8 | 6 | 7 | 4 | 4 | 4 | 9 | 7 | 6 | 8 | 9 | 2 |
| | | | | | | | | | 1 | 3 | | 6 | 2 | 5 | 5 | 6 | 4 | 3 | 1 | 9 | 5 | 4 | 7 | 8 | |
| 6 (19 d.a.t.) | 3 | 5 | 6 | 6 | 4 | 7 | 8 | | 5 | 6 | 4 | 8 | 6 | 8 | 8 | 9 | 5 | 3 | 5 | 9 | 8 | 7 | 9 | 9 | |
| | | | | | | | | | 1 | 3 | 1 | 7 | 2 | 6 | 7 | 8 | 4 | 2 | 1 | 9 | 6 | 4 | 8 | 9 | |
| 7 | | | | | | | | | 5 | 2 | | 6 | 3 | 9 | 8 | 8 | 6 | | 1 | 7 | | | 5 | 4 | |
| | | | | | | | | | 1 | 2 | | 6 | 3 | 6 | 7 | 6 | 5 | | | 6 | | | 4 | 3 | |
| 8 | | | 4 | 3 | 2 | 3 | | | 5 | 3 | 2 | 8 | 6 | 8 | 8 | 7 | 6 | 1 | | 8 | 3 | | 5 | 5 | |
| | | | | | | | | | 1 | 2 | 1 | 5 | 3 | 6 | 8 | 7 | 5 | 1 | | 7 | 1 | | 5 | 3 | |
| 9 | | | | | | | | | 5 | 4 | | 6 | 3 | 4 | 7 | 7 | 4 | | | 7 | 3 | | 7 | 6 | 1 |
| | | | | | | | | | 1 | 2 | | 5 | 2 | 3 | 6 | 6 | 4 | | | 7 | 2 | | 6 | 5 | 1 |
| 10 | | | | | | | | | 5 | 3 | | 4 | 2 | 4 | 7 | 8 | 4 | 2 | 2 | | | | 5 | 4 | |
| | | | | | | | | | 1 | 3 | | 3 | 1 | 3 | 7 | 6 | 3 | 1 | 1 | | | | 4 | 3 | |
| 11 | | 2 | 2 | 1 | 1 | | | | 5 | 4 | | 6 | 4 | 6 | 9 | 8 | 4 | | | 4 | 4 | | | 5 | 8 |
| | | | | | | | | | 1 | 3 | | 2 | 2 | 5 | 8 | 6 | 3 | | | 1 | 1 | | | 3 | 3 |
| 12 | | 3 | 1 | | 1 | 2 | | | 5 | 4 | | 4 | 4 | 5 | 5 | 8 | 4 | | | 4 | 4 | 3 | 3 | | |
| | | | | | | | | | 1 | 2 | | 2 | 2 | 3 | 3 | 6 | 3 | | | 1 | | | | | |
| 13 | | | | | | | | | 5 | 4 | | 3 | 3 | 6 | 5 | 7 | 5 | | | 5 | 1 | | | 2 | 6 |
| | | | | | | | | | 1 | 2 | | 2 | 1 | 3 | 3 | 4 | 4 | | | 2 | | | | 1 | 2 |
| 14 | 2 | | 4 | 2 | 3 | 2 | 4 | 2 | 5 | 5 | 2 | 8 | 4 | 7 | 8 | 9 | 5 | 3 | 3 | 9 | 4 | 2 | 9 | 9 | 1 |
| | | | | | | | | | 1 | 3 | | 4 | 2 | 6 | 7 | 8 | 4 | 1 | 1 | 8 | 3 | 1 | 9 | 8 | |
| 14 (19 d.a.t.) | 2 | | 3 | 2 | 4 | 2 | 3 | 2 | 5 | 6 | 2 | 9 | 3 | 8 | 9 | 9 | 7 | 3 | | 9 | 3 | 2 | 9 | 9 | |
| | | | | | | | | | 1 | 3 | 1 | 4 | 2 | 6 | 8 | 8 | 5 | 1 | | 8 | 3 | | 8 | 9 | |
| 15 | | | | | | | | | 5 | 4 | | 3 | 3 | 5 | 5 | 6 | 4 | | | 1 | | | | | |
| | | | | | | | | | 1 | 3 | | 2 | 1 | 2 | 3 | 4 | 4 | | | 1 | | | | | |
| 16 | | | | | | | | | 5 | 2 | | 3 | | 1 | 5 | 5 | 4 | | | | | | | | |
| | | | | | | | | | 1 | 1 | | 1 | | | 2 | 2 | 3 | | | | | | | | |
| 17 | | | | | | | | | 5 | 1 | | 3 | 2 | 4 | 7 | 5 | 4 | | | | | | | 5 | 3 |

TABLE 2-continued

| Compound of Ex. No. | Soil drench 10/kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 18 | 4 | 2 | 4 | 3 | 3 | 4 | 3 | 2 | 5 | 4 | 4 | 8 | 7 | 7 | 9 | 9 | 6 | 4 | 3 | 9 | 5 | 4 | 9 | 9 | 3 |
| | | | | | | | | | 1 | 2 | | 7 | 3 | 6 | 7 | 9 | 5 | 3 | | 7 | 3 | 2 | 8 | 8 | |
| 19 | | 1 | 4 | 2 | | 3 | 3 | | 5 | 4 | | 8 | 4 | 7 | 7 | 9 | 7 | 3 | | 9 | 4 | 3 | 7 | 9 | 2 |
| | | | | | | | | | 1 | 2 | | 7 | 2 | 6 | 7 | 8 | 5 | 2 | | 7 | 2 | 1 | 7 | 7 | |
| 20 | | | 3 | 3 | | | | | 5 | 4 | 4 | 8 | 5 | 7 | 8 | 9 | 6 | 4 | 3 | 8 | 5 | 3 | 8 | 9 | |
| | | | | | | | | | 1 | 3 | 1 | 7 | 3 | 6 | 8 | 9 | 5 | 3 | 1 | 7 | 4 | 1 | 6 | 8 | |
| 21 | 1 | 1 | 4 | 2 | | 2 | | | 5 | 2 | 2 | 8 | 4 | 7 | 8 | 9 | 5 | 3 | | 8 | 3 | 2 | 6 | 7 | 2 |
| | | | | | | | | | 1 | 1 | 1 | 3 | 2 | 5 | 6 | 7 | 4 | 1 | | 5 | 1 | | 4 | 1 | |
| 22 | | | 2 | | | 1 | | 3 | 5 | 2 | 1 | 6 | 4 | 7 | 8 | 8 | 6 | 3 | | 6 | 1 | | 5 | 6 | |
| | | | | | | | | | 1 | 1 | | 3 | 2 | 5 | 6 | 5 | 5 | 1 | | 3 | | | 3 | 2 | |
| 23 | | 2 | 5 | 4 | 3 | 4 | 3 | 3 | 5 | 3 | 2 | 7 | 4 | 8 | 8 | 9 | 6 | 4 | 2 | 7 | 3 | 3 | 7 | 8 | 2 |
| | | | | | | | | | 1 | 2 | 1 | 5 | 2 | 7 | 8 | 8 | 6 | 2 | 1 | 5 | 2 | | 6 | 3 | |
| 24 | | | | | | | | | 5 | 2 | | 2 | 1 | 6 | 7 | 5 | 3 | 2 | | 6 | 1 | 1 | 6 | 7 | |
| | | | | | | | | | 1 | 2 | | | | 5 | 7 | 4 | 2 | 1 | | 4 | | | 5 | 7 | |
| 25 | | | | | | | | | 5 | 4 | | 1 | | | 4 | 7 | | | | | | | | | |
| | | | | | | | | | 1 | 2 | | | | | 1 | 5 | | | | | | | | | |
| 29 | 6 | 6 | 7 | 7 | 2 | 5 | 7 | 2 | 5 | 7 | 5 | 8 | 7 | 8 | 9 | 9 | 8 | 7 | 6 | 9 | 8 | 7 | 9 | 9 | 3 |
| | | | | | | | | | 1 | 4 | 1 | 8 | 5 | 7 | 9 | 9 | 6 | 6 | 3 | 9 | 7 | 6 | 9 | 9 | 1 |
| 30 | 6 | 4 | 6 | 6 | 1 | 4 | 5 | 2 | 5 | 7 | 4 | 8 | 6 | 8 | 9 | 9 | 8 | 5 | 5 | 9 | 7 | 7 | 9 | 9 | 1 |
| | | | | | | | | | 1 | 3 | | 7 | 4 | 7 | 9 | 9 | 6 | 3 | 1 | 9 | 5 | 3 | 8 | 9 | |
| 31 | | 4 | 6 | 6 | 3 | 5 | 4 | 6 | 5 | 3 | 1 | 7 | 4 | 7 | 8 | 6 | 6 | 3 | 3 | 8 | 4 | 4 | 7 | 4 | |
| | | | | | | | | | 1 | 1 | 1 | 3 | 2 | 5 | 7 | 4 | 3 | 1 | | 3 | 1 | | 4 | | |

By way of comparison, the following compounds of Table 3 below were made by techniques similar to those described above, and tested in identical biological tests.

TABLE 3

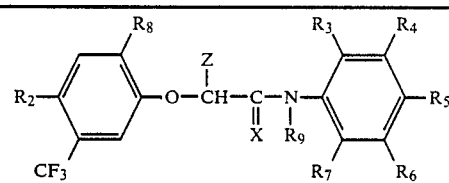

TABLE 3-continued

| Comparison Example | R₂ | R₈ | Z | R₃ | R₄ | R₅ | R₆ | R₇ | R₉ | X |
|---|---|---|---|---|---|---|---|---|---|---|
| C8 | H | F | C₂H₅ | F | H | F | H | H | H | O |
| C9 | H | H | C₂H₅ | H | H | H | H | H | CH₃ | O |

The results of the biological tests (12/13 d.a.t.) are set out in Table 4 below.

TABLE 4

| Compound of Ex. No. | Soil drench 10/kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| C1 | 2 | 0 | 0 | 0 | 8 | 3 | 6 | 4 | 5 | 3 | 0 | 4 | 2 | 9 | 7 | 7 | 8 | 0 | 8 | 3 | 3 | 7 | 6 | 9 | 5 |
| | | | | | | | | | 1 | 0 | 0 | 2 | 1 | 9 | 6 | 6 | 8 | 0 | 2 | 1 | 2 | 5 | 4 | 9 | * |
| C2 | | | 3 | 2 | | | | | 5 | | | 1 | | 5 | 5 | 5 | 3 | | | 4 | | | 3 | | |
| | | | | | | | | | 1 | | | | | 3 | 5 | 3 | 3 | | | 1 | | | 1 | | |
| C3 | | | 3 | | | | | | 5 | 1 | | 4 | 2 | 3 | 5 | 5 | 4 | | | 5 | | | 4 | | * |
| | | | | | | | | | 1 | | | | | 3 | 5 | 4 | 4 | | | 2 | | | 3 | | |
| C4 | | | | | | | | | 5 | | | | | | 4 | 3 | 4 | | | | | | | | |
| | | | | | | | | | 1 | | | | | | 2 | 1 | 3 | | | | | | | | |
| C5 | | | | | | | | | 5 | | | 4 | 3 | 4 | 5 | 5 | 4 | 1 | | 5 | | | 2 | 1 | |
| | | | | | | | | | 1 | 1 | | 1 | | | 2 | 2 | 2 | | | 2 | | | | | |
| C6 | | | 2 | 1 | 1 | 3 | | | 5 | 3 | | 7 | 5 | 7 | 7 | 6 | 6 | 2 | | 8 | 4 | | 4 | 2 | |
| | | | | | | | | | 1 | 1 | | 5 | 3 | 4 | 5 | 4 | 4 | | | 5 | 2 | | 3 | 2 | |
| C7 | | | 6 | 2 | | | | | 5 | 2 | | 4 | 4 | 4 | 8 | 6 | 4 | | | 7 | 2 | | 3 | 4 | |
| | | | | | | | | | 1 | 1 | | 2 | 2 | 1 | 6 | 4 | 2 | | | 5 | | | 2 | 2 | |
| C8 | | | | | | | | | 5 | 1 | | 3 | 2 | 6 | 6 | 4 | 6 | | | 2 | | | 2 | | |
| | | | | | | | | | 1 | | | 1 | 1 | 4 | 4 | 2 | 6 | | | | | | 1 | | |
| C9 | | | | 1 | 4 | 5 | 2 | 3 | 5 | | | | | | | | | 5 | | 5 | 7 | 6 | 7 | 4 | |
| | | | | | | | | | 1 | | | | | | | | | | | 1 | 2 | 3 | 2 | 2 | |

| | | | | | | | | | | |
|---|---|---|---|---|---|---|---|---|---|---|
| C1 | Cl | H | CH₃ | F | H | F | H | H | H | O |
| C2 | H | H | C₂H₅ | F | H | H | H | F | H | O |
| C3 | H | H | C₂H₅ | F | H | F | H | F | H | O |
| C4 | H | H | C₂H₅ | F | F | F | F | F | H | O |
| C5 | H | H | i-C₃H₇ | F | H | H | H | H | H | O |
| C6 | H | H | n-C₃H₇ | F | H | F | H | H | H | O |
| C7 | H | H | n-C₃H₇ | F | H | F | H | H | H | S |

Considering the biological results for these comparison compounds, in comparison with those of the compounds of the invention, the following is noted:

Example C1 is the exact propionic acid lower homologue of Example 2. The respective summated values for the soil drench, foliar spray (5 kg/ha), foliar spray (1 kg/ha), pre-emergence (5 kg/ha) and pre-emergence (1 kg/ha) tests for Example C1 are 23, 40, 32, 41 and 23 (with one result absent), and for Example 2, at 12/13 d.a.t., 25, 51, 41, 49 and 38, in each case higher. Examples C5, C6 and C7 are pentanoic acid analogues of compounds of the invention and are also of poorer activity than their analogues. Examples C8 are C9 and analogues of Examples 6 and 1 respectively, differing only in respect of the position of the fluorine atom in the phenoxy moiety, and the nature of the group $R_9$, respectively, and are of lower activity than their analogues. Examples C2, C3 and C4 differ from compounds of the present invention in having 2, 6-substitution of the anilide moiety and shown moderate activity only in foliar spray applications to the broad-leaved plants coded L, M, SB and S, being substantially inactive in other applications.

I claim:

1. A compound of formula I

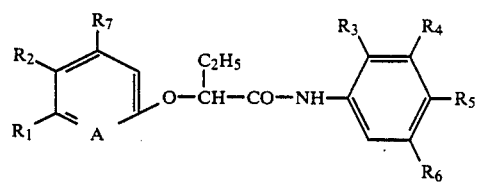

wherein $R_1$ represents a chlorine atom or a trifluoromethyl, difluoromethoxy or acetyl group;
$R_2$ represents a hydrogen chlorine or fluorine atom;
$R_7$ represents a hydrogen atom, or an alkyl or trifluoromethyl group;
$R_3$ represents a hydrogen, chlorine or fluorine atom;
$R_4$ represents a hydrogen or chlorine atom or a trifluoromethyl group;
$R_5$ represents a hydrogen, chlorine or fluorine atom or an alkyl group;
$R_6$ represents a hydrogen or fluorine atom or a trifluoromethyl, alkyl or alkoxy group; and
A represents a nitrogen atom or a —CH— group.

2. A compound as claimed in claim 1, wherein A represents a —CH— group, and $R_7$ represents a hydrogen atom.

3. A compound as claimed in claim 1 in which $R_1$ represents a trifluoromethyl group, $R_2$ represents a chlorine or fluorine atom, $R_3$ and $R_5$ each represent a fluorine atom, $R_4$ and $R_6$ each represent a hydrogen atom and A represents a —CH— group.

4. A herbicidal composition comprising at least one carrier and a compound of formula I

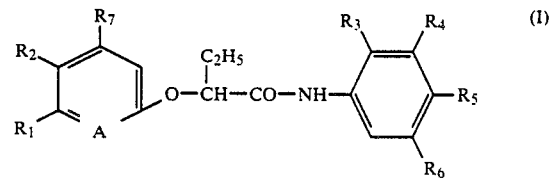

wherein $R_1$ represents a chlorine atom or a trifluoromethyl, difluoromethoxy or acetyl group;
$R_2$ represents a hydrogen chlorine or fluorine atom;
$R_7$ represents a hydrogen atom, or an alkyl or trifluoromethyl group;
$R_3$ represents a hydrogen, chlorine or fluorine atom;
$R_4$ represents a hydrogen or chlorine atom or a trifluoromethyl group;
$R_5$ represents a hydrogen, chlorine or fluorine atom or an alkyl group;
$R_6$ represents a hydrogen or fluorine atom or a trifluoromethyl, alkyl or alkoxy group; and
A represents a nitrogen atom or a —CH— group.

5. A method of combating undesired plant growth at a locus, said method comprising treating the locus with an effective amount of a compound, of formula I

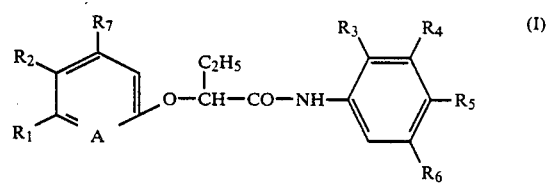

wherein $R_1$ represents a chlorine atom or a trifluoromethyl, difluoromethoxy or acetyl group;
$R_2$ represents a hydrogen chlorine or fluorine atom;
$R_7$ represents a hydrogen atom, or an alkyl or trifluoromethyl group;
$R_3$ represents a hydrogen, chlorine or fluorine atom;
$R_4$ represents a hydrogen or chlorine atom or a trifluoromethyl group;
$R_5$ represents a hydrogen, chlorine or fluorine atom or an alkyl group;
$R_6$ represents a hydrogen or fluorine atom or a trifluoromethyl, alkyl or alkoxy group; and
A represents a nitrogen atom or a —CH— group.

* * * * *